United States Patent [19]
Torre

[11] 4,306,568
[45] Dec. 22, 1981

[54] METHOD AND APPARATUS FOR CONGELATION CRYOMETRY IN CRYOSURGERY

[76] Inventor: Douglas P. Torre, 22 E. 36th St., New York, N.Y. 10016

[21] Appl. No.: 100,148

[22] Filed: Dec. 4, 1979

[51] Int. Cl.$^3$ .............................................. A61B 5/05
[52] U.S. Cl. ................................. 128/734; 128/303.1
[58] Field of Search ..................... 128/734, 736, 303.1, 128/399, 741

[56] References Cited

U.S. PATENT DOCUMENTS

| | | | |
|---|---|---|---|
| 2,763,935 | 9/1956 | Whaley et al. | 128/734 X |
| 3,830,226 | 8/1974 | Staub et al. | 128/741 |
| 3,866,600 | 2/1975 | Rey | 128/734 |
| 3,948,269 | 4/1976 | Zimmer | 128/303.1 |
| 4,140,109 | 2/1979 | Savic et al. | 128/734 |
| 4,207,897 | 6/1980 | Lloyd et al. | 128/303.1 |
| 4,252,130 | 2/1981 | Le Pivert | 128/734 |

OTHER PUBLICATIONS

Wooley-Hart, "A Simple Technique . . . Conductivity", Med. & Biol. Eng., vol. 10, pp. 561-563, 1972.
Zacarian, S. A., Cryosurgical Advances in Dermat. and Tumors of The Head and Neck, 3-9 (1977).
LePivert, P. J., J. Dermat. Surg. Oncol. 3, 395-397 (1977).
Savic, M.; Zacarian, S. A.; J. Dermat. Surg. Oncol. 3, 592-593 (1977).
Gage A.; Caruna J. A.; Cryobiology 17, 1-7 (1980).

*Primary Examiner*—Lee S. Cohen
*Attorney, Agent, or Firm*—Hubbell, Cohen, Stiefel & Gross

[57] ABSTRACT

A method and apparatus for measuring the temperature of malignant tissue to be frozen during cryosurgery, involving the insertion of an active needle electrode (18) laterally of and below the malignant tumor (T or T') to be treated, applying an indifferent electrode (20) to the patient's skin (S) at a point displaced from the tumor, applying a low voltage D.C. potential (12) across the electrodes to pass a current of less than 20 microamperes through the tissue, and monitoring (16) the current decrease during freezing to determine the point at which to terminate the freeze treatment with cryocongelation of all the malignant tissue but without substantial destruction of the underlying tissue.

8 Claims, 4 Drawing Figures

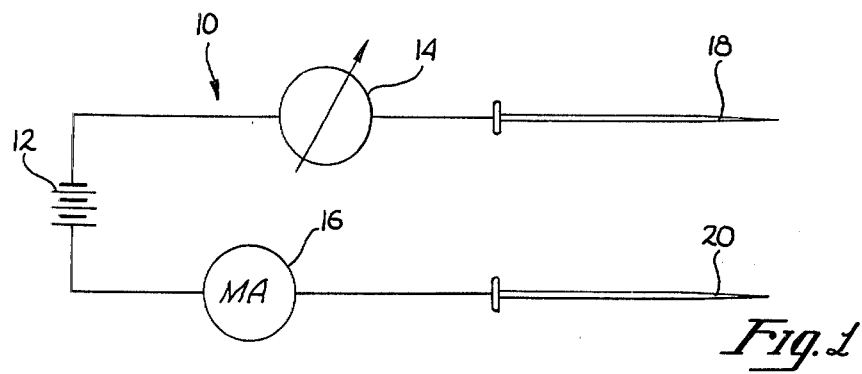
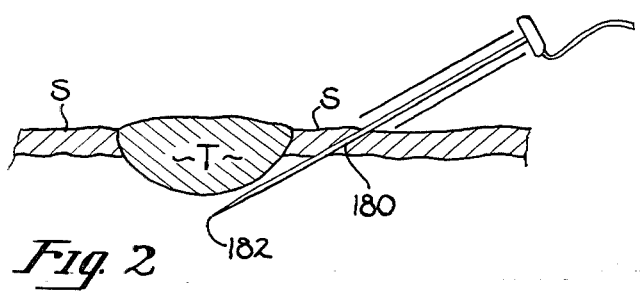
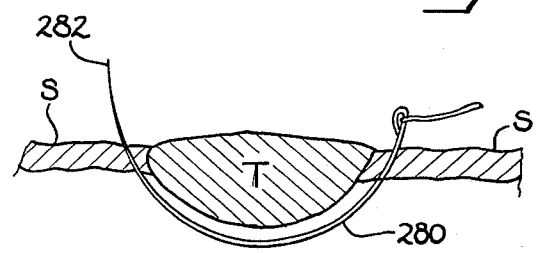
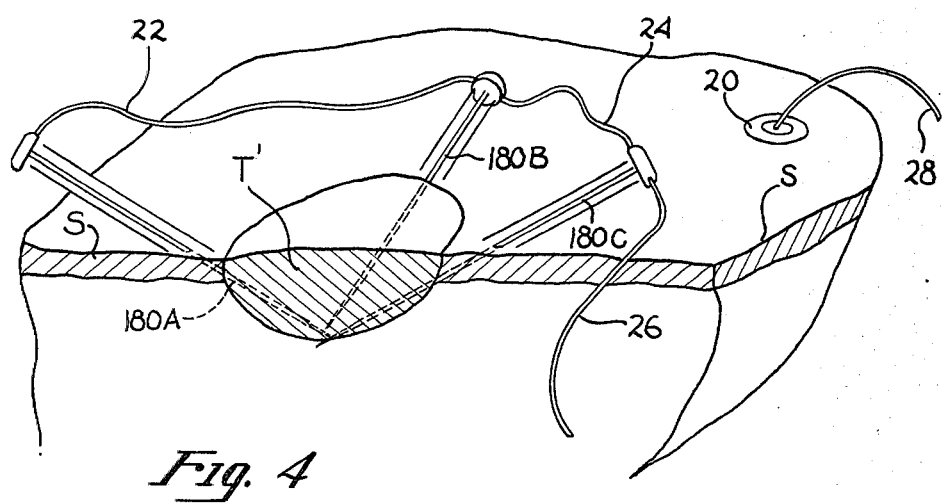

METHOD AND APPARATUS FOR CONGELATION CRYOMETRY IN CRYOSURGERY

DESCRIPTION

Technical Field

The present invention relates to an improved technique for determining the degree of cryocongelation of malignant tissue during cryosurgery, and more particularly to such a technique involving the monitoring of the temperature of the tumor to be frozen by measuring the decrease of a D.C. electric current conducted therethrough.

Cryosurgery has been widely utilized in recent years for the treatment of skin cancer. Such surgery involves the treatment with cryoprobes chilled by liquid nitrogen, cone-sprays of liquid nitrogen, or like techniques for freezing and destroying the malignant tissue while attempting to insure as little injury to the adjacent nonmalignant cells as possible.

Most surgeons recommend the freezing of routine basal cell carcinomas by inducing temperatures of about −25° C. at the deep margins of such malignant tissues, and advocate the use of two or more freeze-thaw cycles to insure the cryocongelation thereof. In the treatment of metastasizing malignancies or other deep carcinomas some cryosurgeons require freeze temperatures of from −40° to −60° C. to insure complete cryocongelation. In view of this criticality, it is essential for the surgeon to know that the proper "depth dose" of freeze has been provided to insure total destruction of the malignant tissue without undue damage to the surrounding normal tissue.

With the preceding in mind a number of techniques have heretofore been proposed for measuring and monitoring freeze temperatures produced during cryosurgery. The most commonly used technique initially employed for monitoring such temperatures involved the application of a thermocouple inserted within or below the neoplasm and recorded on a pyrometer (Zacarian, S. A., "Cryosurgical Advances in Dermatology and Tumors of the Head and Neck", 3-9, 1977,). This method has however been found seriously wanting in terms of accuracy.

It has also been suggested that freeze temperatures in cryosurgery may be monitored by the measurement of low frequency electrical impedance between pairs of needle electrodes inserted adjacent the tissue targeted for destruction by freezing (Le Pivert, P. J., "The Measurement of Low Frequency Electrical Impedance As A Guide To Effective Cryosurgery", J. Dermatol. Surg. Oncol. 3: 395-397, 1977). Le Pivert utilized a 220 volt A.C. source, and disclosed that impedances of between 0.5 and 10 megohms indicated adequate cryocongelation. It has subsequently been determined that the Le Pivert apparatus does not in fact accurately reflect the temperature of the tissue between the electrodes thereof, but rather only the temperature in the immediate vicinity of the respective needle electrodes.

An alternative impedance measurement technique has also been described in the literature, involving the measurement of the impedance between a single needle electrode inserted directly into a malignant tumor and a second, remote contact electrode placed about the patient's wrist or the like (Savic, M. and Zacarian, S. A., "A New Impedance-Based Method For Controlled Cryosurgery Of Malignant Tumors", J. Dermatol. Surg. Oncol. 3: 592-593, 1977; U.S. Pat. No. 4,140,109).

The Savic et al., device utilizes a 110 volt alternating current source and measures the impedance between the malignant tissue immediately adjacent the tip of the needle electrode and the unfrozen tissue adjacent the remote contact electrode.

It is among the objects of the present invention to provide an improved method and apparatus for monitoring the temperature of malignant tissue to be treated by cryosurgery, which is more accurate and safer to utilize than the previously proposed thermal or impedance-based measurement techniques described hereinabove.

DISCLOSURE OF INVENTION

In accordance with the present invention, an improved technique is provided for monitoring the temperature of malignant tissue to be subjected to cryocongelation, which comprises inserting an active needle electrode laterally of and below a tumor to be treated, applying an indifferent electrode to the patients' skin at a point displaced from the tumor, applying a low voltage D.C. potential across said electrodes to pass a current of less than about 20 microamperes between the electrodes, and measuring the decrease of current during cryosurgery to determine the temperature of the tissue at the base of the tumor and to thereby monitor the degree of cryocongelation thereof. The current decrease during freezing may thus be monitored to a value of no more than about 5 microamperes (equivalent to a temperature in the malignant tissue adjacent the active needle electrode of no more than about −22° to −25° C.), at which freezing of principal tissue electrolytes (e.g., NaCl) has occurred. Such treatment is adequate to effect cryocongelation of routine basal cell carcinomas. Alternatively, the current decrease may be monitored to a value of no more than about one microampere (equivalent to a temperature in the malignant tissue adjacent the active needle electrode of about −40° to −60° C.) to insure total cryocongelation of even metasticized malignancies or other deep carcinomas.

The relatively simple method and apparatus of the present invention may be employed without the risks inherent in use of the previously proposed impedance-based measurement systems. Thus, the present method requires only the imposition of a low voltage D.C. potential, e.g., as low as 1.5 or 3 volts, as distinguished from the 110 volt or 220 volt A.C. potentials applied by the prior techniques. Similarly, the present method involves minimal conducting currents which do not exceed about 20 microamperes, and which may be less than 10 microamperes, in order to minimize if not preclude any pain or tissue destruction.

Moreover, since the active needle electrode is inserted laterally of and below the tumor to be treated, obstruction of the operative field and penetration of the tumor is minimized, thus simplifying cryosurgical procedures (and facilitating the use of cones or open cylinders to limit spray of the liquid nitrogen freezant), and minimizing the risk of seeding of malignant cells by the needle electrode. Improved access to the malignancy during the freezing operation additionally facilitates removal of the tumor during freezing, thus protecting deeper structures.

Other objects and advantages of the present invention will be apparent from consideration of the following detailed description of preferred embodiments thereof.

BRIEF DESCRIPTION OF THE DRAWING

The details of the present invention will be described in connection with the accompanying drawing, in which:

FIG. 1 is a schematic circuit diagram of a cryometer measuring device of the present invention, showing the active needle electrode applied laterally of the tumor to be treated and the indifferent electrode applied to the skin surface at a point spaced from the tumor;

FIG. 2 is a diagrammatic representation showing the technique or inserting a flexible straight wire active electrode laterally of and below the tumor to be treated;

FIG. 3 is a similar diagrammatic representation showing the technique for inserting a curved active electrode laterally of and below the tumor; and FIG. 4 is yet a further diagrammatic representation showing the technique for connecting a plurality of active needle electrodes in parallel for measurement of the current, and hence the temperature, about the base of a relatively large tumor.

BEST MODE FOR CARRYING OUT THE INVENTION

With reference to FIG. 1, an apparatus 10 for measuring the degree of cryocongelation of malignant tissue is illustrated. The apparatus comprises a low voltage DC power source 12 which may, for example, be a 1½ or 3 volt battery, connected in circuit with a rheostat 14, a microammeter 16 and a pair of electrodes 18 and 20. Electrode 18 is suitably a needle electrode utilized as the active electrode inserted through the patient's skin laterally of and below the malignant tumor to be treated by cryosurgery. The electrode 20, on the other hand, is employed as an indifferent electrode applied to the skin at a point spaced from the operative site, e.g., in the manner of electrodes suitable for EKG procedures. Thus, the indifferent electrode may simply be applied to the skin surface over an electrode paste or other electrically conductive medium utilized to insure a good electrical connection between the electrode and the skin.

As illustrated in FIGS. 2 and 3, the active needle electrode is inserted through the patient's skin S laterally of a tumor T, generally spaced about 1 millimeter therefrom, and angled under the base of the tumor to be subjected to cryosurgery. Thus, as shown in FIG. 2 a flexible, straight wire electrode 180 is inserted through the patient's skin and under the tumor so angled as to minimize, if not entirely avoid, any penetration of the tumor in order to avoid any risk of seeding the cancer cells. The electrode is thus manipulated so that the needle point or tip 182 lies directly below the central portion of tumor T. Such result may of course be readily achieved, knowing the dimensions of the tumor from other diagnostic data, by control of the inclination and depth of insertion of the needle electrode.

Referring now to FIG. 3, a curved active needle electrode 280 is illustrated below the tumor T. Again, knowing the dimensions of the tumor from other diagnostic information the surgeon chooses the particular dimensions of the curved needle electrode to be utilized, inserts the same approximately 1 millimeter laterally of tumor T, and "threads" the needle under the tumor. The electrode needle point or tip 282 thus extends outwardly from the skin S at a point spaced about 1 millimeter from the side of Tumor T remote from the point of insertion thereof. It will be understood that large diameter needle electrodes may be thus utilized for large tumors and smaller diameter needle electrodes for smaller tumors, the surgeon pinching or otherwise distorting the anatomy and/or tilting the needle electrode 280 to vary the needle depth and the surface diameter subtended by the needle arch for any particular needle and/or tumor size.

Use of the flexible straight wire needle electrode 180 or the curved needle electrode 280 shown in FIGS. 2 and 3, and particularly the latter, enables the surgeon to "cradle" the lesion and thus provide accurate monitoring of the marginal surfaces of the base of tumor T upon cryogenic treatment thereof. In accordance with this particularly preferred form of the invention, accurate measurements and monitoring of the temperature of the malignant tissue is thus obtained, whereby to insure accurate cryocongelation thereof.

FIG. 4 illustrates the insertion of a plurality of straight active needle electrodes 180a, 180b and 180c laterally of and below various points on the periphery of a relatively large tumor T'. Electrodes 180a, 180b and 180c are connected in parallel by wires 22, 24 and 26, the latter of which is connected to the external D.C. cryometer device (see FIG. 1). At the same time, indifferent electrode 20 is connected by conductor 28 to the measurement device to complete the circuit. In this manner, the maximum current flowing between any of electrodes 180a, 180b or 180c to the control electrode 20 may be measured, in order to ascertain the maximum temperature at any point about the base of the relatively large tumor T'. The extent of the cryogenic treatment may thus be controlled to insure total cryocongelation of the malignant tissue while minimizing the degree of destruction of normal tissue.

In operation, when the cryometer circuit of FIG. 1 is completed with electrodes 18 and 20 attached to the patient accurate monitoring of freeze temperatures produced during cryosurgery is achieved. Thus, as the tissue in the region of tumor T or T' is frozen, the current measured by the microammeter 16 decreases from an initial value (set by rheostat 14 at no more than 20 microamperes, or even less than 10 microamperes) to no more than 5 microamperes, 1 microampere, or even less. The surgeon may thus directly monitor the temperature in the region of the base of the tumor (where the highest relative temperature will be found) to insure that the freeze treatment is continued for a period sufficient to destroy the malignant tissue without, however, substantial destruction of adjacent normal tissue. Thus, as indicated hereinabove, in the treatment of routine basal cell carcinomas the cryogenic treatment may be terminated when the cryometer current is reduced to about 5 microamperes (equivalent to a temperature of about $-22°$ to $-25°$ C. adjacent the base of the tumor). Similarly, in the treatment of metasticized malignancies the surgeon may continue cryogenic treatment until the current measured by the device 10 is 1 microampere or less, to insure freeze treatment of the base of the tumor at about $-40°$ to $-60°$ C. and consequent complete cryocongelation thereof.

There is thus provided, in accordance with the present invention, an improved technique for measuring and monitoring the freeze temperatures obtained about the base of malignant tissue during cryosurgery. The method and apparatus utilized herein is simple, portable, and economical. Moreover, it is quite safe, necessitating only the use of minimum voltages and currents and thus not imposing any risk of pain or tissue destruction. Moreover, by inserting the active needle electrode thereof laterally of and below the tumor to be treated and utilizing a flexible straight wire or curved needle electrode, it is possible to monitor the tumor freeze temperatures without obstructing the operative site and without seeding of malignant cells.

It will be understood that various changes may be made in the preferrred embodiments of the invention described hereinabove without departing from the scope of the method and apparatus hereof. Accordingly, the preceding description is intended as illustrative only, the scope of the present invention to be determined only by the claims appended hereto.

I claim:

1. In the cryocongelation of malignant tissue, the improvement which comprises monitoring the temperature of the tissue to be frozen by inserting an active needle electrode laterally of and below a tumor to be treated, applying an indifferent electrode to the patient's skin at a point displaced from said tumor, applying a low voltage D.C. potential across said electrodes to pass a current of less than 20 microamperes between said electrodes, and measuring the decrease of current during freezing to determine the temperature of the tissue at the base of the tumor and to thereby monitor the degree of cryocongelation thereof.

2. The method of claim 1, in which the decrease of current during freezing is monitored to a current value of no more than five microamperes which is equivalent to a temperature in the tissue adjacent the active needle electrode of no more than $-22°$ to $-25°$ C., below the eutectic point for common cellular electrolytes.

3. The method of claim 1, in which the decrease of current during freezing is monitored to a current value of no more than one microampere which is equivalent to a temperature in the tissue adjacent the active needle electrode of no more than $-40°$ to $-60°$ C., below the eutectic point for all cellular electrolytes.

4. The method of claim 1, wherein the active needle electrode comprises a flexible straight wire electrode and in which said wire electrode is inserted adjacent the tumor and so angled as to avoid penetration thereof, the point of the needle lying directly below the central portion of the tumor.

5. The method of claim 1, wherein the active needle electrode possesses a generally concave curvature and in which said needle electrode is so inserted adjacent the tumor as to pass thereunder to cradle the same, the point of the needle electrode extending outwardly from the skin at a point adjacent the side of the tumor remote from that adjacent the point of insertion of said electrode.

6. An apparatus for measuring the degree of cryocongelation of malignant tissue, which comprises a plurality of independently movable active needle electrodes for subcutaneous insertion laterally of and below a tissue to be treated at different points spaced about the periphery thereof without invading said tissue, an indifferent electrode for application to the patient's skin at a point displaced from said tissue, a low voltage D.C. power source in circuit with said electrodes, having a pair of output terminals, circuit means for simultaneously connecting said plurality of active electrodes to one of said output terminals, circuit means for connecting said indifferent electrode to the other of said output terminals, current regulating means for producing a current in said circuit of less than 20 microamperes, and meter means in said circuit for monitoring said current.

7. An apparatus for measuring the degree of cryocongelation of malignant tissue, which comprises a flexible straight wire electrode for non-malignant tissue invasive insertion adjacent and under the tumor to be cryocongelated, an indifferent electrode for application to the patient's skin at a point displaced from such tissue, a low voltage D.C. power source in circuit with said electrodes, current regulating means for producing a current in said circuit of less than 20 microamperes, and meter means in said circuit for monitoring said current.

8. An apparatus for measuring the degree of cryocongelation of malignant tissue, which comprises an active needle electrode possessing a generally concave curvature for inserting peripherally of and under the tissue to be cryocongelated without invading the malignant tissue, an indifferent electrode for application to the patient's skin at a point displaced from said tissue, a low voltage D.C. power source in circuit with said electrodes, current regulating means for producing a current in said circuit of less than 20 microamperes, and meter means in said circuit for monitoring said current.

* * * * *